United States Patent
Simonyan et al.

(10) Patent No.: US 12,257,063 B2
(45) Date of Patent: Mar. 25, 2025

(54) OBJECTIVE EVALUATION OF NEUROLOGICAL MOVEMENT DISORDERS FROM MEDICAL IMAGING

(71) Applicant: MASSACHUSETTS EYE AND EAR INFIRMARY, Boston, MA (US)

(72) Inventors: Kristina Simonyan, Weston, MA (US); Davide Valeriani, Boston, MA (US)

(73) Assignee: MASSACHUSETTS EYE AND EAR INFIRMARY, Boston, MA (US)

(*) Notice: Subject to any disclaimer, the term of this patent is extended or adjusted under 35 U.S.C. 154(b) by 222 days.

(21) Appl. No.: 17/765,177

(22) PCT Filed: Sep. 30, 2020

(86) PCT No.: PCT/US2020/053571
§ 371 (c)(1),
(2) Date: Mar. 30, 2022

(87) PCT Pub. No.: WO2021/067457
PCT Pub. Date: Apr. 8, 2021

(65) Prior Publication Data
US 2022/0369999 A1    Nov. 24, 2022

Related U.S. Application Data

(60) Provisional application No. 62/964,469, filed on Jan. 22, 2020, provisional application No. 62/908,448, filed on Sep. 30, 2019.

(51) Int. Cl.
*A61B 5/00* (2006.01)
*A61B 5/055* (2006.01)
*G06T 7/00* (2017.01)

(52) U.S. Cl.
CPC .......... *A61B 5/4082* (2013.01); *A61B 5/0042* (2013.01); *A61B 5/055* (2013.01);
(Continued)

(58) Field of Classification Search
CPC ..... A61B 5/4082; A61B 5/0042; A61B 5/055; A61B 5/4839; A61B 5/7275;
(Continued)

(56) References Cited

U.S. PATENT DOCUMENTS

2009/0137565 A1*  5/2009  Frucht ............... A61K 31/19
                                                514/270
2013/0012366 A1   1/2013  Seitzer
(Continued)

FOREIGN PATENT DOCUMENTS

WO      2018194778 A1      10/2018
WO      WO-2020223434 A1 * 11/2020 ........... A61B 5/0042

OTHER PUBLICATIONS

Sivaranjini et al: "Deep learning based diagnosis of Parkinson's disease using convolutional neural network", Multimedia Tools and Applications, Kluwer Academic Publishers, Boston, US, vol. 79, No. 21-22, Mar. 21, 2019 (Mar. 21, 2019), pp. 15467-15479. (Year: 2019).*

(Continued)

*Primary Examiner* — Keith M Raymond
*Assistant Examiner* — Patrick M Mehl
(74) *Attorney, Agent, or Firm* — Tarolli, Sundheim, Covell & Tummino LLP (57) ABSTRACT

Systems and methods are provided for evaluating a patient for a neurological movement disorder. A three-dimensional medical image of a brain of the patient is captured and provided to an artificial neural network having at least one convolutional layer to provide a set of output values. The set of output values is provided to a machine learning model to provide a clinical parameter representing one of a presence of the neurological movement disorder in the patient and a response of the patient to a specific treatment for the neurological movement disorder.

10 Claims, 5 Drawing Sheets

(52) U.S. Cl.
CPC .......... *A61B 5/4839* (2013.01); *G06T 7/0012* (2013.01); *G06T 2207/10088* (2013.01); *G06T 2207/20081* (2013.01); *G06T 2207/20084* (2013.01)

(58) Field of Classification Search
CPC ... A61B 5/4848; A61B 5/7267; G06T 7/0012; G06T 2207/10088; G06T 2207/20081; G06T 2207/20084; G06T 2207/30016; A61N 2/006; A61N 5/0622
See application file for complete search history.

(56) References Cited

U.S. PATENT DOCUMENTS

| | | | |
|---|---|---|---|
| 2015/0026520 | A1 | 1/2015 | Zhou et al. |
| 2018/0028969 | A1 | 2/2018 | Karavolos |
| 2018/0267997 | A1* | 9/2018 | Lin ........................ G06F 16/951 |
| 2019/0282829 | A1 | 9/2019 | Cassano et al. |
| 2019/0286953 | A1* | 9/2019 | Farhadi .................. G06N 3/045 |
| 2021/0082565 | A1* | 3/2021 | Kraft ..................... G16H 50/20 |
| 2021/0174937 | A1* | 6/2021 | Swisher ................. G16H 50/20 |
| 2021/0327563 | A1* | 10/2021 | He ........................ G06V 10/462 |

OTHER PUBLICATIONS

Tamilarasi et al. 2020 IEEE Xplore Jul. 2020 Proceedings of the Fifth International Conference on Communication and Electronics Systems (ICCES 2020) p. 1208-1212 (Year: 2020).*

Valeriani et al. 2020 PNAS 117:26398â26405 ; Pub. Date Oct. 20, 2020 (Year: 2020).*

Wang SH, Tang C, Sun J, Yang J, Huang C, Phillips P, Zhang YD. Multiple Sclerosis Identification by 14-Layer Convolutional Neural Network With Batch Normalization, Dropout, and Stochastic Pooling. Front Neurosci. Nov. 8, 2018;12:818. doi: 10.3389/fnins.2018. 00818. PMID: 30467462; PMCID: PMC6236001.

Redlich R, Opel N, Grotegerd D, Dohm K, Zaremba D, Bürger C, Münker S, Mühlmann L, Wahl P, Heindel W, Arolt V, Alferink J, Zwanzger P, Zavorotnyy M, Kugel H, Dannlowski U. Prediction of Individual Response to Electroconvulsive Therapy via Machine Learning on Structural Magnetic Resonance Imaging Data. JAMA Psychiatry. Jun. 1, 2016;73(6):557-64. doi: 10.1001/jamapsychiatry. 2016.0316. PMID: 27145449.

Shah, Pir Masoom, et al. "Detection of Parkinson disease in brain MRI using convolutional neural network." 2018 24th International Conference on Automation and Computing (ICAC). IEEE, 2018.

International Search Report for Corresponding Application Serial No. PCT/US2020/053571.

Sivaranjini Set al: "Deep learning based diagnosis of Parkinson's disease using convolutional neural network", Multimedia Tools and Applications, Kluwer Academic Publishers, Boston, US, vol. 79, No. 21-22, Mar. 21, 2019 (Mar. 21, 2019), pp. 15467-15479, XP037156203, ISSN: 1380-7501, DOI: 10.1007/SII042-019-7469-8 [retrieved on Mar. 21, 2019].

Wang Shui-Hua et al: "Multiple Sclerosis Identification by 14-Layer Convolutional Neural Network With Batch Normalization, Dropout, and Stochastic Pooling", Frontiers in Neuroscience, [Online] vol. 12, 2018, p. 81800818, XP055818203, DOI: 10.3389/fnins. 2018.00818 Retrieved from the Internet: URL:https://www.ncbi. nlm.nih.gov/pmc/articles/PMC6236001/pdf/fnins-12-00818.pdf> [retrieved on Jan. 26, 2023].

Soheil Esmaeilzadeh et al: "End-to-End Parkinson Disease Diagnosis using Brain MR-Images by 3D-CNN", arxiv.org, Cornell University Library, 201 Olin Library Cornell University Ithaca, NY 14853, Jun. 13, 2018 (Jun. 13, 2018), XP080890442.

Zhang Yu-Dong et al: "Multiple sclerosis identification by convolutional neural network with dropout and parametric ReLU", Journal of Computational Science, Elsevier, Amsterdam, NL, vol. 28, Jul. 9, 2018 (Jul. 9, 2018), pp. 1-10, XP085507846, ISSN: 1877-7503, DOI: 10.1016/J.JOCS.2018.07.003.

Shah Pir Masoom et al: "Detection of Parkinson Disease in Brain MRI using Convolutional Neural Network", 2018 24th International Conference on Automation and Computing (ICAC), Chinese Automation and Computing Society in the UK—CACSUK, Sep. 6, 2018 (Sep. 6, 2018), pp. 1-6, XP033571409, DOI: 10.23919/ICONAC. 2018.8749023 [retrieved on Jun. 27, 2019].

Li Fei-Fei et al: "Lecture 8—Feb. 1, 2016 9 Lecture 8: Spatial Localization and Detection", Feb. 1, 2016 (Feb. 1, 2016), p. 1, XP093018126, Retrieved from the Internet: URL:http://cs231n. stanford.edu/slides/2016/winter1516_1ecture8.pdf [retrieved on Jan. 26, 2023].

Anonymous: "Medikamentose Behandlung bei 5,6,15 Parkinson-Krankheit", Jun. 19, 2019 (Jun. 19, 2019), XP093018180, Retrieved from the Internet: URL:https://www.gesundheitsinformation.de/ medikamentoese-behandlung-bei-parkinson-krankheit.html [retrieved on Jan. 26, 2023]. English translation not provided.

Anonymous: "Nicht medikamentose Behandlung bei Parkinson-Krankheit", Jun. 19, 2019 (Jun. 19, 2019), XP093018269, Retrieved from the Internet: URL:https://www.gesundheitsinformation.de/ nicht-medikamentoese-behandlung-bei-parkinson-krankheit.html [retrieved on Jan. 27, 2023]. English translation not provided.

Extended European Search Report dated Oct. 10, 2023 for corresponding Application No. 20871026.9-1210/4037550 PCT/US2020053571.

Communication pursuant to Rules 70(2) and 70a(2) EPC dated Oct. 27, 2023 for corresponding Application No. 20871026.9-1210/ 4037550 PCT/US2020053571.

Current claims for Application No. PCT/US2020053571.

* cited by examiner

FIG. 7

OBJECTIVE EVALUATION OF NEUROLOGICAL MOVEMENT DISORDERS FROM MEDICAL IMAGING

RELATED APPLICATIONS

This application claims priority from each of U.S. Provisional Application No. 62/908,448, filed 30 Sep. 2019 and U.S. Provisional Application No. 62/964,469, filed 22 Jan. 2020. The subject matter of each of these applications is incorporated herein by reference in its entirety.

GOVERNMENT FUNDING

This invention was made with government support under grant nos. DC011805 and DC012545 awarded by the National Institute of Deafness and Other Communication Disorders (NIDCD) and grant no. NS08816 awarded by the National Institutes of Health. The government has certain rights in this invention.

TECHNICAL FIELD

This invention relates to medical imaging, and more specifically, to evaluation of diagnosis and treatment outcomes from medical imaging.

SUMMARY

In accordance with an aspect of the present invention, a method is provided for evaluating a patient for a neurological movement disorder. A three-dimensional medical image of a brain of the patient is captured and provided to an artificial neural network having at least one convolutional layer to provide a set of output values. The set of output values is provided to a machine learning model to provide a clinical parameter representing one of a presence of the neurological movement disorder in the patient and a response of the patient to a specific treatment for the neurological movement disorder.

In accordance with another aspect of the present invention, a system is provided for evaluating a patient for a neurological movement disorder. The system includes a processor and a non-transitory computer readable medium storing instructions for evaluating a three-dimensional medical image of a brain of the patient. The instructions are executable by the processor to provide an imager interface that receives a three-dimensional medical image from an associated imager, a convolutional neural network that provides a set of output values from the three-dimensional medical image of the brain of the patient, and a machine learning model that provides a clinical parameter relating to the neurological movement disorder for the patient from the set of output values.

In accordance with a further aspect of the present invention, a method is provided for diagnosing dystonia. A three-dimensional raw, or unprocessed, magnetic resonance image of a brain of an individual is captured and provided to a convolutional neural network to provide a set of output values. The set of output values is provided to a machine learning model to provide a clinical parameter representing the presence of dystonia in the patient.

DETAILED DESCRIPTION

A "patient", as used herein, can refer to any human or warm-blooded animal that is being evaluated by a clinician as part of the provisional of medical care or the performance of a clinical trial.

A "clinical parameter," as used herein, is any continuous, ordinal, or categorical parameter that represents a current or predicted future medical condition of a patient, and can include any value representing diagnosis of disease or injury or predicting a patient outcome or response to treatment.

A "clinical parameter relating to a neurological movement disorder" can include any parameter representing the presence of a neurological movement disorder in the patient, the presence of a disease or disorder for which a neurological movement disorder is a symptom, the presence of a specific type of a neurological movement disorder in the patient, the presence of a disease or disorder that co-occurs with a neurological movement disorder, the likelihood that a patient will respond to a specific treatment for a neurological movement disorder, and the presence of a specific biomarker associated with a neurological movement disorder in the patient.

A "clinical parameter relating to dystonia" can include any parameter representing the presence of dystonia in the patient, the presence of a disease or disorder for which dystonia is a symptom, the presence of a specific type of dystonia in the patient, the presence of a disease or disorder that co-occurs with dystonia, the likelihood that a patient will respond to a specific treatment for dystonia, and the presence of a specific biomarker associated with dystonia in the patient.

A "convolutional neural network," as used herein, is any artificial neural network having at least one convolutional layer.

A "non-linear transfer function" refers to any transfer or activation function applied within an artificial neural network to produce an output from a given node or sequence of nodes that is not a linear function of the sum of the inputs to the node or sequence of nodes. Examples include the sigmoid function, the hyperbolic tangent function, and a rectifier function.

An "image of a brain", as used herein, refers to any medical image of at least a portion of the human brain.

A "raw MR image," as used herein, refers to an image that is generated at a magnetic resonance imaging system prior to any preprocessing of the image.

A "neurological movement disorder," as used herein, is a neurological condition that causes abnormal, increased or reduced, voluntary or involuntary movements in a patient. Examples include dystonia, Parkinson's disease, parkinsonism, tremor, ataxias, tics, Tourette syndrome, Huntington's disease, myoclonus, chorea, progressive supranuclear palsy, restless legs syndrome, tardive dyskinesia, multiple system atrophy, Wilson's disease, and functional movement disorders.

Systems and methods provided herein utilize a machine learning model incorporating a convolutional neural network for evaluating a patient for the presence of a neurological movement disorder. The systems and methods provided herein utilize a 3-D convolutional neural network to extract relevant features from clinical medical imaging of the brain, from which more detailed disease-specific, microstructural parameters representing neurological movement disorders can be derived. Using this method, an objective diagnosis of neurological movement disorders can be achieved with significant accuracy. In one implementation of the claimed systems and methods applied to diagnosis of dystonia, an area under a receiver operating characteristic (ROC) curve (AUC) of over ninety-two percent and an accuracy of over ninety-eight percent were achieved for the trained model on independent test sets. The sensitivity of the system is ninety-five percent, the specificity is eighty-five percent, the positive predicted value exceeds eighty-six percent, and the negative predicted value exceeds ninety-four percent.

Figure 1:
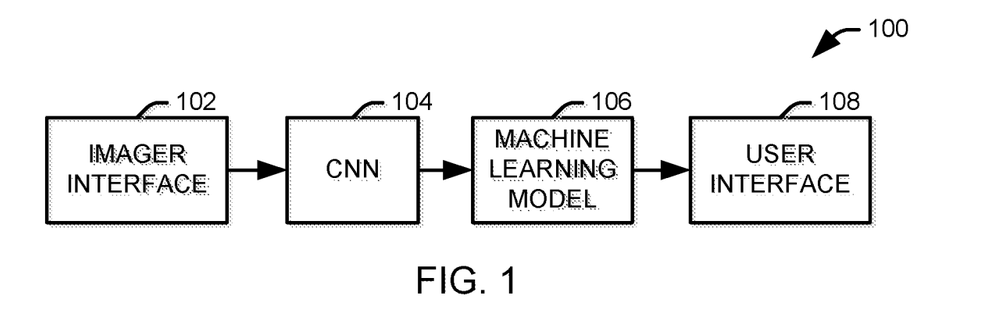
FIG. 1 illustrates a system for assigning a clinical parameter relating to a neurological movement disorder to a patient.

FIG. 1 illustrates a system 100 for assigning a clinical parameter relating to a neurological movement disorder to a patient. The system 100 can be implemented, for example, as software instructions stored on a non-transitory computer readable medium and executed by an associated processor to evaluate a provided three-dimensional medical image of a brain of the patient that is a structural magnetic resonance (MR) image, functional magnetic resonance (MR) image, computer tomography (CT) image, positron emission tomography (PET) image, electroencephalogram (EEG), or magnetoencephalogram (MEG). The system 100 includes an imager interface 102 that receives the three-dimensional medical image from an associated imager (not shown), such as a magnetic resonance (MR) imager, a computed tomography (CT) scanner, a positron emission tomography (PET) scanner, a magnetoencephalography (MEG) scanner, or an encephalograph system. It will be appreciated that the imager interface 102 can receive the image directly from the imager or indirectly by retrieving a stored image from the imager from a local or remote storage medium. In one implementation, the imager interface 102 can apply various digital image preprocessing techniques, such as skull stripping, edge enhancement, Gaussian smoothing, and similar techniques, to the medical image to facilitate analysis of the image at a convolutional neural network (CNN) 104. In one implementation, the imager interface 102 receives a raw structural MR image and provides the raw MR image to the convolutional neural network without preprocessing.

The convolutional neural network 104 processes the three-dimensional medical image to provide a set of output values representing the brain of the patient. The convolutional neural network 104 utilizes one or more convolutional layers to automatically identify and extract features relevant to evaluating the patient for diagnosis and treatment of a neurological movement disorder. In one implementation, the convolutional network comprises a plurality of convolutional units, each receiving a three-dimensional input and producing a feature map representing a convolutional filter, or kernel, applied to the input. Each unit includes a convolutional layer that generates, at each node, a linear combination of a selected set of inputs to the convolutional layer, an activation layer that applies a non-linear transfer function to the output of each node in the convolutional layer, and a pooling layer that reduces the dimensionality of the output of the activation layer. In one example, a max-pooling layer is used to make the learned features invariant to changes in scale and rotation.

The convolutional units are arranged as to analyze the image in a plurality of parallel streams, with each stream comprising a plurality of convolutional units. The feature map generated by each convolutional unit within a stream can be provided as an input to a next convolutional unit within a stream, such that the various convolutional units within a given stream evaluate the image at different levels of detail. Convolutional units at the same ordinal location within the parallel streams, referred to herein as sets, can have different convolutional kernels as to extract different features from the input. The output of each stream can be provided to a global max pooling layer to provide the set of output values.

A machine learning model 106 provides a clinical parameter relating to a neurological movement disorder for the patient from the set of output values provided by the convolutional neural network 104. A clinical parameter relating to a neurological movement disorder can include any parameter relating to the presence of a neurological movement disorder in the patient, the presence of a disease or disorder for which a neurological movement disorder is a symptom, the presence of a specific type of a neurological movement disorder in the patient, the presence of a disease or disorder that co-occurs with a given neurological movement disorder, a proposed treatment for a neurological movement disorder, the likelihood that a patient will respond to a specific treatment for a neurological movement disorder, and the presence of a specific biomarker associated with a neurological movement disorder in the patient. It will be appreciated that the clinical parameter can be categorical or continuous. For example, a given parameter can directly predict a state of the patient as a categorical parameter, represent a likelihood of a given state of the patient as a continuous parameter, or represent ranges of likelihoods as categorical parameters.

In one example, the clinical parameter is a categorical parameter representing a proposed therapy for the patient, such as a botulinum toxin injection, an anticholinergic drug, a dopaminergic drug, a GABAergic drug, sodium oxybate, deep brain stimulation, non-invasive brain stimulation, rehabilitation, or physical therapy. In another example, the clinical parameter represents a type of dystonia, such as isolated (also known as idiopathic or primary) dystonia, including focal dystonia, segmental dystonia, multifocal dystonia, hemidystonia, generalized dystonia, as well as combined or dystonia-plus (also known as secondary) dystonia, tardive dystonia, paroxysmal disorders, Dopa-responsive dystonia, rapid-onset dystonia parkinsonism, and Wilson's disease. In another example, the clinical parameter represents a differential diagnosis with other neurological movement disorders, such as Parkinson's disease, parkinsonism, tremor, ataxias, tics, Tourette syndrome, Huntington's disease, myoclonus, chorea, progressive supranuclear palsy, restless legs syndrome, tardive dyskinesia, multiple system atrophy, Wilson's disease, and functional movement disorders. In another example, the clinical parameter represents at least one location on the three-dimensional medical image at which the machine learning model has determined that a biomarker for the neurological movement disorder is present.

The machine learning model 106 can utilize one or more pattern recognition algorithms, implemented, for example, as classification and regression models, each of which analyze the extracted feature vector to assign the clinical parameter to the user. Where multiple classification and regression models are used, the machine learning model 106 can include an arbitration element, which can be utilized to provide a coherent result from the various algorithms. Depending on the outputs of the various models, the arbitration element can simply select a class from a model having a highest confidence, select a plurality of classes from all models meeting a threshold confidence, select a class via a voting process among the models, or assign a numerical parameter based on the outputs of the multiple models. Alternatively, the arbitration element can itself be implemented as a classification model that receives the outputs of the other models as features and generates one or more output classes for the patient.

The machine learning model 106, as well as any constituent models, can be trained on training data representing the various classes of interest. The training process of the machine learning model 106 will vary with its implementation, but training generally involves a statistical aggregation of training data into one or more parameters associated with the output classes. For rule-based models, such as decision trees, domain knowledge, for example, as provided by one or more human experts, can be used in place of or to supplement training data in selecting rules for classifying a user using the extracted features. Any of a variety of techniques can be utilized for the models, including support vector machines (SVMs), regression models, self-organized maps, fuzzy logic systems, data fusion processes, boosting and bagging methods, rule-based systems, or artificial neural networks (ANNs).

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. An SVM classifier utilizes a user-specified kernel function to organize training data within a defined feature space. In the most basic implementation, the kernel function can be a linear function, although the systems and methods described herein can utilize any of a number of linear or non-linear kernel functions.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

Many ANN classifiers are fully-connected and feedforward. A convolutional neural network, however, includes convolutional layers in which nodes from a previous layer are only connected to a subset of the nodes in the convolutional layer. Recurrent neural networks are a class of neural networks in which connections between nodes form a directed graph along a temporal sequence. Unlike a feedforward network, recurrent neural networks can incorporate feedback from states caused by earlier inputs, such that an output of the recurrent neural network for a given input can be a function of not only the input but one or more previous inputs. As an example, Long Short-Term Memory (LSTM) networks are a modified version of recurrent neural networks, which makes it easier to remember past data in memory.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used, but a continuous parameter can be computed according to a number of decision trees that select a given task.

A regression model applies a set of weights to various functions of the extracted features, most commonly linear functions, to provide a continuous result. In general, regression features can be categorical, represented, for example, as zero or one, or continuous. In a logistic regression, the output of the model represents the log odds that the source of the extracted features is a member of a given class. In a binary classification task, these log odds can be used directly as a confidence value for class membership or converted via the logistic function to a probability of class membership given the extracted features.

In one example, the machine learning model 106 is implemented as an artificial neural network that includes a first layer, which is dense (i.e., fully-connected), that receives the set of output values from the convolutional neural network, and a second layer that applies a non-linear activation function to the outputs of the first layer. The output of the second layer is provided to a third layer, which is also dense, and a softmax layer provides a value representing the clinical parameter from the output of the third layer. Regardless of the specific model employed, the clinical parameter generated at the machine learning model 106 can be provided to a user at an output device (not shown) via a user interface 108 or stored on a non-transitory computer readable medium, for example, in an electronic medical record associated with the patient.

Figure 2:
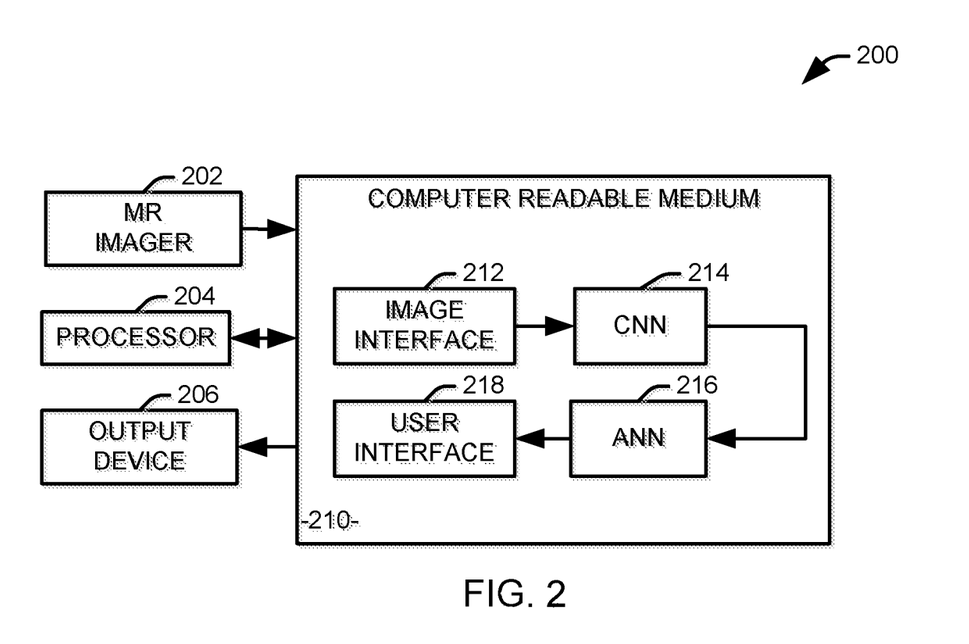
FIG. 2 illustrates an example implementation of a system for assigning a clinical parameter relating to dystonia from a raw, three-dimensional magnetic resonance image.

FIG. 2 illustrates an example implementation of a system 200 for assigning a clinical parameter relating to dystonia from a raw, three-dimensional (3-D) magnetic resonance (MR) image. Currently, there is no objective test for dystonia, and work continues on establishing clinical protocols for diagnosing various presentations of the disorder. See, e.g., *Expert Recommendations for Diagnosing Cervical, Oromandibular, and Limb Dystonia*, by Defazio et al., *Neurological Sciences* 40:89-95 (2019). Studies have indicated that as many as half of all people with dystonia are undiagnosed or misdiagnosed, suggesting that the incidence of dystonia is much higher than currently known. No validated diagnostic biomarkers are available to allow for a more objective diagnosis. Id. at pg. 90, first paragraph. In fact, clinical imaging in patients with dystonia is generally normal without findings of gross radiological abnormalities, although research studies have shown that microscopic abnormalities in certain areas of the brain are present in patients with dystonia. See, e.g., *Dystonia* by Balint et al., *Nature Reviews Disease Primers*, Volume 4, Article No. 25 (2018); See also Neuroimaging applications in dystonia by Simonyan K., *Int Rev Neurobiol* 2018; 143:1-30. As a result, current clinical procedures for diagnosing dystonia frequently involve a lengthy, uncertain process of eliminating other potential causes for the patient's symptoms until an appropriate differential diagnosis can be made.

The system 200 includes an MR imager 202, a processor 204, an output device 206, and a non-transitory memory 210 storing computer executable instructions for assessing coronary microvascular dysfunction for a patient. The machine executable instructions include, for example, an image interface 212 that is configured to receive the raw 3-D MR image from the MR imager 202, a remote system storing medical images, or a local storage medium. Depending on the source of the images, the image interface 212 can include, for example, software for interacting with appropriate hardware for implementing a bus or network connection with the source of the sequence of images.

A convolutional neural network (CNN) 214 receives the raw 3-D MR image from the image interface 212 and generates a set of output values representing structural features of the brain relating to biomarkers for dystonia. In the illustrated example, the CNN 214 includes thirty channels, each applying a different set of convolutional filters to the raw MR image. The CNN 214 of the illustrated example has four convolutional layers, each followed by a Rectified Linear Unit (ReLU) activation layer and a max pooling layer to form what is referred to herein as a "convolutional unit". A first convolutional unit uses a 6×6×6 kernel for the convolutional layer and a 4×4×4 kernel for the pooling layer. The second and third convolutional units utilize 3×3×3 kernels for both the convolutional and pooling layers, and the fourth convolutional unit utilizes 2×2×2 kernels for both the convolutional and pooling layers. The output of the fourth convolutional unit is provided to a global max pooling layer to provide a maximum value for the feature map produced for each channel as the set of output values.

An artificial neural network (ANN) 216 generates a clinical parameter relating to dystonia from the set of output values provided by the CNN 214. In practice, the clinical parameter can be any continuous or categorical parameter useful in the diagnosis or treatment of dystonia or a co-occurring condition, such as essential tremor or Parkinson's disease. In the illustrated example, the clinical parameter is a categorical parameter that can assume a first value, representing the presence of dystonia, a second value, representing an absence of dystonia, or a third value, representing uncertainty in the diagnosis and a need to refer the patient for further examinations. The CNN 214 and the ANN 216 can be trained together on samples labeled to indicate whether they represent the presence or absence of dystonia.

In the illustrated example, the ANN 216 includes a dense layer followed by a ReLU activation layer. The output of the ReLU activation layer is provided to another dense layer, having nodes representing output classes (e.g., "dystonia present" and "dystonia absent"), and the output of this layer is provided to a softmax layer to generate values representing probabilities for each class by comparing the probability that dystonia is present to a set of one or more threshold values. From these probabilities and a set of two threshold values, a categorical parameter representing the presence, absence, or uncertain presence of dystonia can be determined. In the illustrated example, the thresholds were selected such that less than ten percent of test images were classified into the "uncertain" class. The categorical parameter can be displayed to a user at the output device 206 via a user interface 218.

The system 200 has been used to diagnose dystonia in patients with high accuracy, ranging between ninety-eight and one hundred percent for various types of dystonia. Further, the system 200 is designed to be computationally efficient, completing the analysis of a given image using less than one hundred fifty thousand floating point operations. In one example of the illustrated implementation of the system 200, the analysis could be performed with only one hundred thousand floating point operations. As a result, the analysis is both energy efficient and can be performed in less than a second.

In view of the foregoing structural and functional features described above, example methods will be better appreciated with reference to FIGS. 3-6. While, for purposes of simplicity of explanation, the example methods of FIGS. 3-6 are shown and described as executing serially, it is to be understood and appreciated that the present examples are not limited by the illustrated order, as some actions could in other examples occur in different orders, multiple times and/or concurrently from that shown and described herein. Moreover, it is not necessary that all described actions be performed to implement a method.

Figure 3:
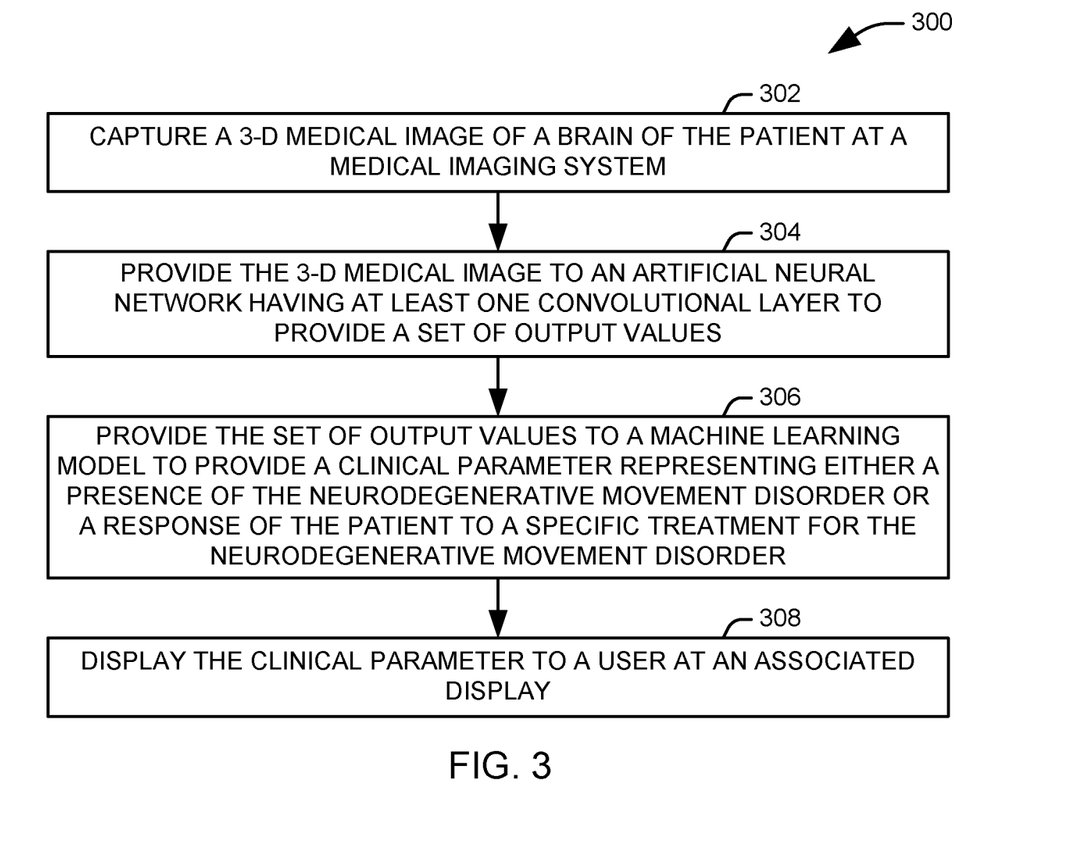
FIG. 3 illustrates a method for evaluating a patient for a neurological movement disorder.

FIG. 3 illustrates a method 300 for evaluating a patient for a neurological movement disorder. At 302, a three-dimensional medical image of a brain of the patient is captured at a medical imaging system. For example, the image can be captured at a magnetic resonance (MR) imager, a computed tomography scanner, a positron emission tomography scanner, a magnetoencephalography scanner, or an encephalograph system. At 304, the three-dimensional medical image of the brain of the patient is provided to an artificial neural network having at least one convolutional layer to provide a set of output values. In one example, the three-dimensional MR image is provided to the artificial neural network as a raw MR image.

At 306, the set of output values are provided to a machine learning model to provide a clinical parameter representing one of a presence of the neurological movement disorder and a response of the patient to a specific treatment for the neurological movement disorder. In one implementation, the machine learning model is implemented as an artificial neural network having at least one fully connected layer. The clinical parameter can represent any current or predicted future neurological movement disorder of a patient, as well as current or predicted responses to treatment for that disorder. In one implementation, the clinical parameter is a continuous parameter representing the likelihood of either the presence of the neurological movement disorder in the patient or a positive response to a specific treatment for the neurological movement disorder. In another implementation, the clinical parameter represents a location on the three-dimensional medical image at which a biomarker for a neurological movement disorder is present. In another implementation, the clinical parameter is a categorical parameter representing a proposed therapy for the patient, such as a botulinum toxin injection, an anticholinergic drug, a dopaminergic drug, a GABAergic drug, sodium oxybate, deep brain stimulation, non-invasive brain stimulation, rehabilitation, and physical therapy. The clinical parameter is displayed to a user at an associated display at 308.

Figure 4:
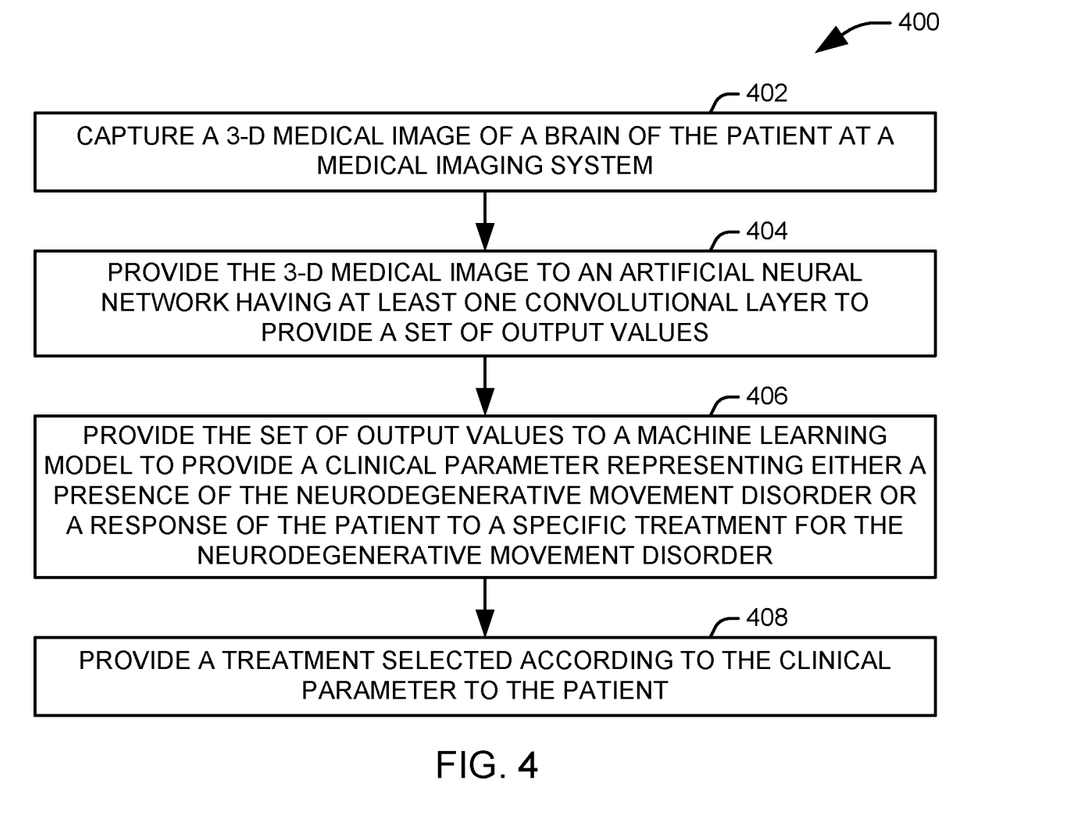
FIG. 4 illustrates a method for treating a patient for a neurological movement disorder.

FIG. 4 illustrates a method 400 for treating a patient for a neurological movement disorder. At 402, a three-dimensional medical image of a brain of the patient is captured at a medical imaging system. At 404, the three-dimensional medical image of the brain of the patient is provided to an artificial neural network having at least one convolutional layer to provide a set of output values. At 406, the set of output values are provided to a machine learning model to provide a clinical parameter representing one of a presence of the neurological movement disorder and a response of the patient to a specific treatment for the neurological movement disorder. At 408, a treatment that is selected according to the clinical parameter is provided to the patient. The treatment can include one or more of a botulinum toxin injection, an anticholinergic drug, a dopaminergic drug, a GABAergic drug, sodium oxybate, deep brain stimulation, non-invasive brain stimulation, rehabilitation, and physical therapy to the patient.

Figure 5:
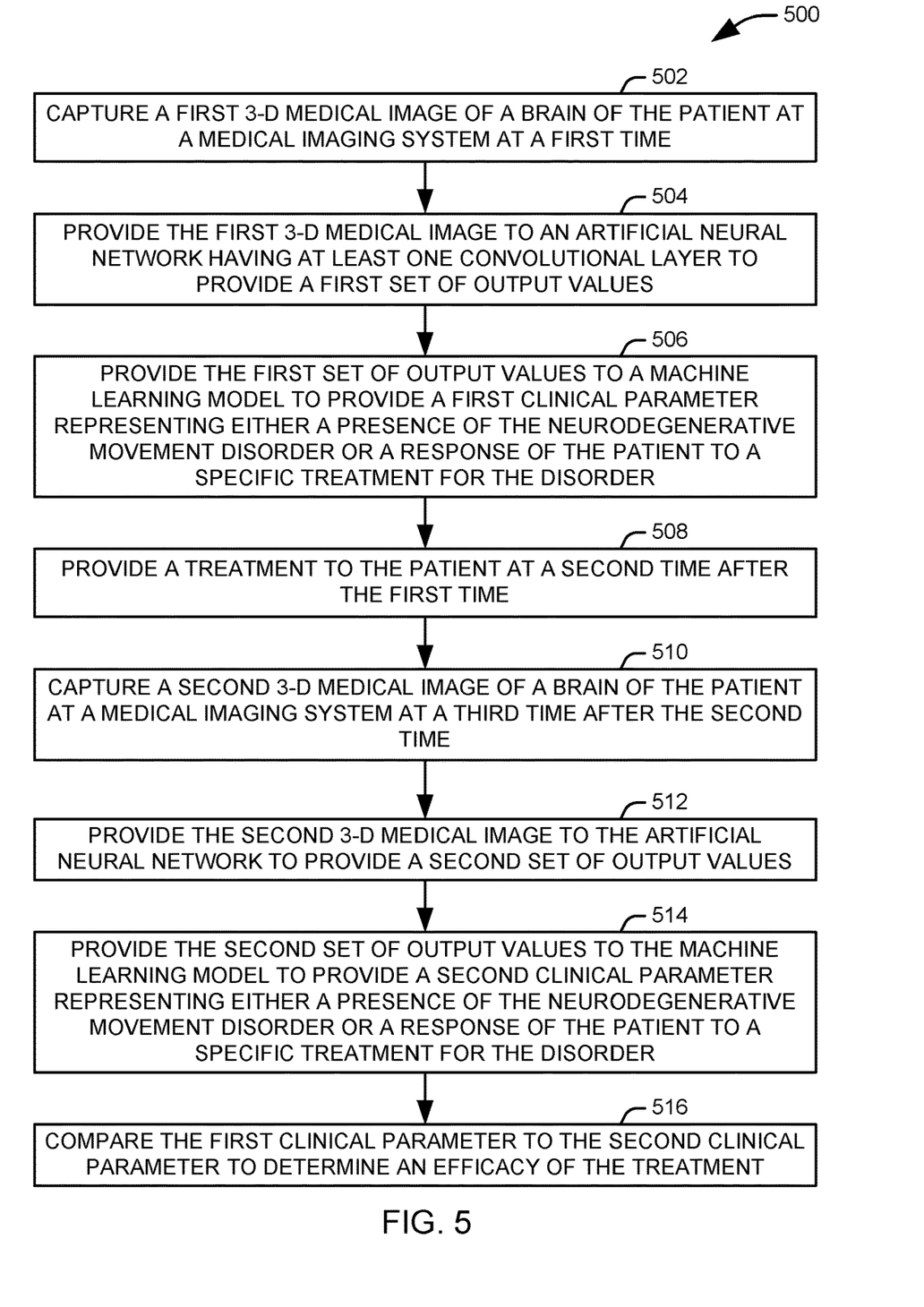
FIG. 5 illustrates a method for evaluating the response of a patient to treatment for a neurological movement disorder.

FIG. 5 illustrates a method 500 for evaluating the response of a patient to treatment for a neurological movement disorder. At 502, a first three-dimensional medical image of a brain of the patient is captured at a medical imaging system at a first time. At 504, the first three-dimensional medical image of the brain of the patient is provided to a convolutional neural network to provide a first set of output values. At 506, the first set of output values are provided to a machine learning model to provide a first clinical parameter representing either a presence of the neurological movement disorder and a response of the patient to a specific treatment for the neurological movement disorder.

At 508, the treatment is provided to the patient at a second time that is after the first time. At 510, a second three-dimensional medical image of a brain of the patient is captured at the medical imaging system at a third time that is after the second time. At 512, the second three-dimensional medical image of the brain of the patient is provided to the convolutional neural network to provide a second set of output values. At 514, the second set of output values are provided to the machine learning model to provide a second clinical parameter representing either the presence of the neurological movement disorder and the response of the patient to a specific treatment for the neurological movement disorder. At 516, the first clinical parameter is compared to the second clinical parameter to determine an efficacy of the treatment.

Figure 6:
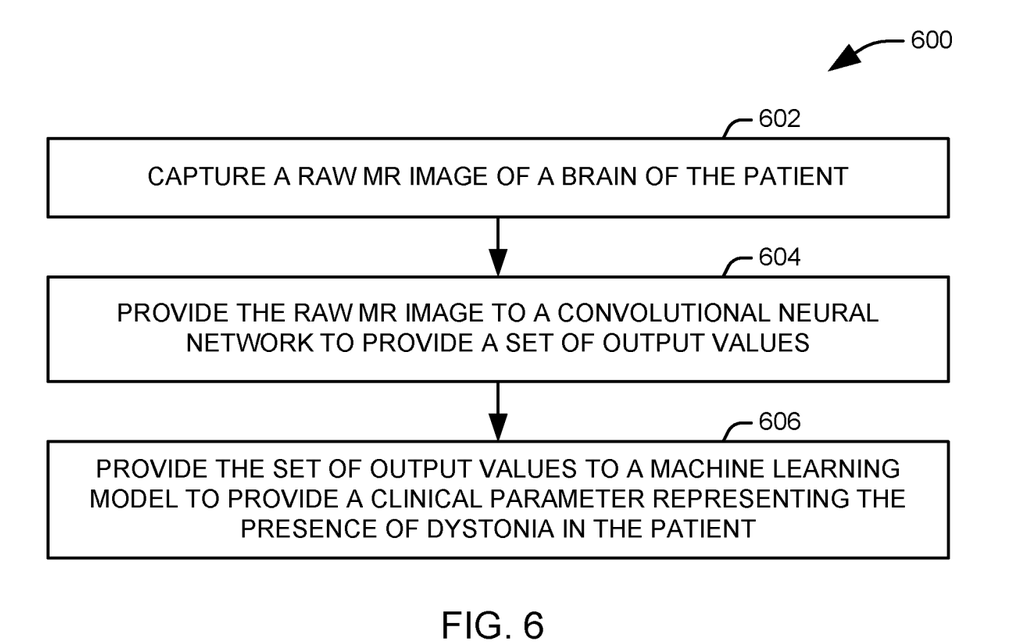
FIG. 6 illustrates a method for diagnosing dystonia.

FIG. 6 illustrates a method 600 for diagnosing dystonia. At 602, a raw magnetic resonance (MR) image of a brain of a patient is captured. At 604, the raw MR image of the brain of the patient is provided to a convolutional neural network to provide a set of output values. At 606, the set of output values is provided to a machine learning model to provide a clinical parameter representing the presence of dystonia in the patient. The clinical parameter can then be displayed to a user or used to select a treatment, if any, to be applied to the patient. In one example, the treatment can include providing any of a botulinum toxin injection, an anticholinergic drug, a dopaminergic drug, a GABAergic drug, sodium oxybate, deep brain stimulation, non-invasive brain stimulation, rehabilitation, and physical therapy to the patient.

In one implementation, the clinical parameter is a categorical parameter that can assume any of a first value, indicating the presence of dystonia, a second value, indicating the absence of dystonia, and a third value, indicating uncertainty in the diagnosis and a need to refer the patient for further examinations. In another example, the clinical parameter is a categorical parameter representing a type of dystonia selected from a group comprising isolated dystonia, focal dystonia, segmental dystonia, multifocal dystonia, hemidystonia, generalized dystonia, combined dystonia, tardive dystonia, paroxysmal disorders, Dopa-responsive dystonia, rapid-onset dystonia parkinsonism, and Wilson's disease. In still another example, the clinical parameter is a continuous parameter representing the likelihood that the patient is experiencing dystonia.

Figure 7:
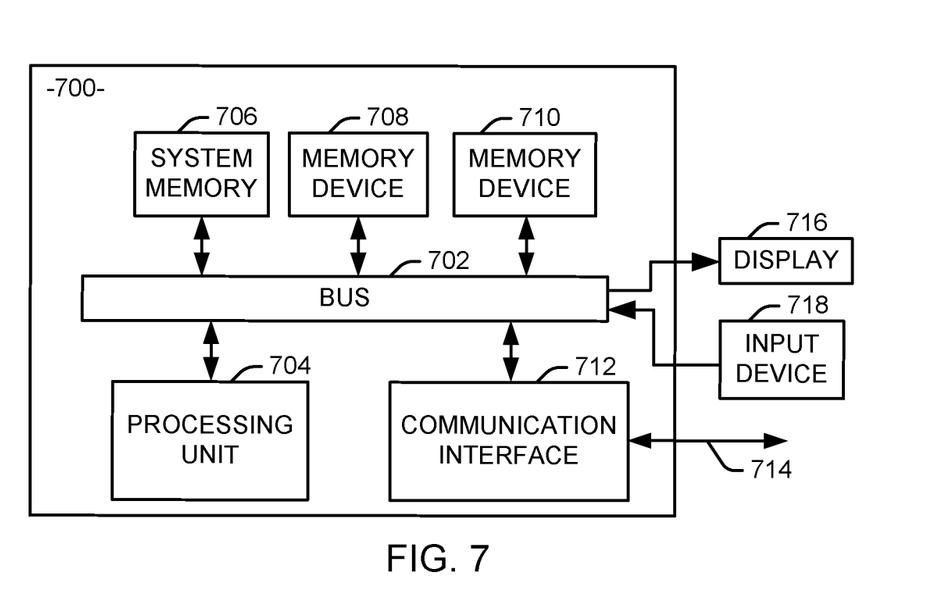
FIG. 7 is a schematic block diagram illustrating an exemplary system of hardware components capable of implementing examples of the systems and methods disclosed herein.

FIG. 7 is a schematic block diagram illustrating an exemplary system 700 of hardware components capable of implementing examples of the systems and methods disclosed herein. The system 700 can include various systems and subsystems. The system 700 can be a personal computer, a laptop computer, a workstation, a computer system, an appliance, an application-specific integrated circuit (ASIC), a server, a server BladeCenter, a server farm, etc.

The system 700 can include a system bus 702, a processing unit 704, a system memory 706, memory devices 708 and 710, a communication interface 712 (e.g., a network interface), a communication link 714, a display 716 (e.g., a video screen), and an input device 718 (e.g., a keyboard, touch screen, and/or a mouse). The system bus 702 can be in communication with the processing unit 704 and the system memory 706. The additional memory devices 708 and 710, such as a hard disk drive, server, standalone database, or other non-volatile memory, can also be in communication with the system bus 702. The system bus 702 interconnects the processing unit 704, the memory devices 706-710, the communication interface 712, the display 716, and the input device 718. In some examples, the system bus 702 also interconnects an additional port (not shown), such as a universal serial bus (USB) port.

The processing unit 704 can be a computing device and can include an application-specific integrated circuit (ASIC). The processing unit 704 executes a set of instructions to implement the operations of examples disclosed herein. The processing unit can include a processing core.

The additional memory devices 706, 708, and 710 can store data, programs, instructions, database queries in text or compiled form, and any other information that may be needed to operate a computer. The memories 706, 708 and 710 can be implemented as computer-readable media (integrated or removable), such as a memory card, disk drive, compact disk (CD), or server accessible over a network. In certain examples, the memories 706, 708 and 710 can comprise text, images, video, and/or audio, portions of which can be available in formats comprehensible to human beings. Additionally or alternatively, the system 700 can access an external data source or query source through the communication interface 712, which can communicate with the system bus 702 and the communication link 714.

In operation, the system 700 can be used to implement one or more parts of a system for evaluating a patient for dystonia in accordance with the present invention. Computer executable logic for implementing the system resides on one or more of the system memory 706, and the memory devices 708 and 710 in accordance with certain examples. The processing unit 704 executes one or more computer executable instructions originating from the system memory 706 and the memory devices 708 and 710. The term "computer readable medium" as used herein refers to a medium that participates in providing instructions to the processing unit 704 for execution. This medium may be distributed across multiple discrete assemblies all operatively connected to a common processor or set of related processors. Specific details are given in the above description to provide a thorough understanding of the embodiments. However, it is understood that the embodiments can be practiced without these specific details. For example, physical components can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps, and means described above can be done in various ways. For example, these techniques, blocks, steps, and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine-readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system for evaluating a patient for a dystonia comprising:
   a processor; and
   a non-transitory computer readable medium storing instructions for evaluating a raw magnetic resonance (MR) image of a brain of the patient, the instructions being executable by the processor to provide:
   an imager interface that receives the raw MR image from an associated imager and provides the raw MR image to the convolutional neural network, such that no preprocessing is applied to the image prior to providing the image to the convolutional neural network;
   a convolutional neural network that provides a set of output values from the raw MR image of the brain of the patient; and a machine learning model that provides a clinical parameter relating to the dystonia for the patient from the set of output values.

2. The system of claim 1, wherein the convolutional neural network and the machine learning model are configured to provide the clinical parameter from the raw MR image using no more than one hundred fifty thousand floating point operations.

3. The system of claim 1, wherein the machine learning model is implemented as an artificial neural network comprising:
   a first layer, which is dense, that receives the set of output values from the convolutional neural network;
   a second layer that applies a non-linear activation function to the outputs of the first layer;
   a third layer, which is dense; and
   a Softmax layer that provides a value representing the clinical parameter from the output of the third layer.

4. The system of claim 1, wherein the convolutional neural network comprises a plurality of convolutional units, each comprising a convolutional layer, an activation layer, and a pooling layer, the plurality of convolutional units comprising:
   a first set of convolutional units that each provide an associated one of a first set of convolutional filters to an instance of the raw MR image;

a second set of convolutional units that each provide an associated one of a second set of convolutional filters to the output of an associated one of the first set of convolutional units;

a third set of convolutional units that each provide an associated one of a third set of convolutional filters to the output of an associated one of the second set of convolutional units;

a fourth set of convolutional units that each provide an associated one of a fourth set of convolutional filters to the output of an associated one of the third set of convolutional units; and a global max pooling layer that provides the set of output values from the output of the fourth set of convolutional units.

5. The system of claim 1, wherein the clinical parameter is a categorical parameter representing a proposed therapy for the patient selected from a group comprising botulinum toxin injection, an anticholinergic drug, a dopaminergic drug, a GABAergic drug, sodium oxybate, deep brain stimulation, non-invasive brain stimulation, rehabilitation, and physical therapy.

6. A method for evaluating a patient for a dystonia comprising:

capturing a raw magnetic resonance (MR) image of a brain of a patient;

providing the raw MR image of the brain of the patient to a convolutional neural network to provide a set of output values, such that no preprocessing is applied to the image prior to providing the image to the convolutional neural network; and providing the set of output values to a machine learning model to provide a clinical parameter representing the presence of dystonia in the patient.

7. The method of claim 6, wherein the clinical parameter is a categorical parameter that can assume any of a first value, indicating the presence of dystonia, a second value, indicating the absence of dystonia, and a third value, indicating uncertainty in the diagnosis and a need to refer the patient for further examinations.

8. The method of claim 6, further comprising providing one of a botulinum toxin injection, an anticholinergic drug, a dopaminergic drug, a GABAergic drug, sodium oxybate, deep brain stimulation, non-invasive brain stimulation, rehabilitation, and physical therapy to the patient.

9. The method of claim 6, wherein the clinical parameter is a categorical parameter representing a type of dystonia selected from a group comprising isolated dystonia, focal dystonia, segmental dystonia, multifocal dystonia, hemidystonia, generalized dystonia, combined dystonia, tardive dystonia, paroxysmal disorders, Dopa-responsive dystonia, rapid-onset dystonia parkinsonism, and Wilson's disease.

10. The method of claim 6, wherein the clinical parameter is a continuous parameter representing the likelihood that the patient is experiencing dystonia.

* * * * *